United States Patent
Ghetzler et al.

(10) Patent No.: US 6,289,741 B1
(45) Date of Patent: Sep. 18, 2001

(54) MOLDING DEVICE AND METHOD FOR MEASURING THE BONDING STRENGTH OF ELASTOMERS

(75) Inventors: Richard Ghetzler, Buffalo Grove; Michael A. Mast, Palatine; Neil E. Hodge, Evanston; Nate Newman, Winnetka; Jeff Browning, Chicago, all of IL (US)

(73) Assignee: Northrop Grumman Corporation, Los Angeles, CA (US)

( * ) Notice: Subject to any disclaimer, the term of this patent is extended or adjusted under 35 U.S.C. 154(b) by 0 days.

(21) Appl. No.: 09/315,562

(22) Filed: May 20, 1999

(51) Int. Cl.$^7$ ........................................... G01N 3/08
(52) U.S. Cl. ............................................. 73/827; 73/150 A
(58) Field of Search ................... 73/150 A, 827; 29/402.11, 888.02

(56) References Cited

U.S. PATENT DOCUMENTS

| | | | |
|---|---|---|---|
| 3,628,378 | 12/1971 | Regan | 73/93 |
| 3,821,892 | 7/1974 | Saberg | 73/88 B |
| 4,263,811 | 4/1981 | Shaw | 73/827 |
| 4,567,758 * | 2/1986 | Fisher et al. | 73/150 A |
| 4,586,371 | 5/1986 | Ivie et al. | 73/150 A |
| 4,606,225 * | 8/1986 | Thomason et al. | 73/150 A |
| 4,893,513 | 1/1990 | Schroeder et al. | 73/827 |
| 5,313,841 | 5/1994 | Layher | 73/827 |
| 5,361,639 | 11/1994 | Thorsen | 73/827 |
| 5,649,447 | 7/1997 | Van Avery | 73/150 A |

* cited by examiner

Primary Examiner—Benjamin R. Fuller
Assistant Examiner—Maurice Stevens
(74) Attorney, Agent, or Firm—Terry J. Anderson; Karl J. Hoch, Jr.

(57) ABSTRACT

A novel device and method for the injection and molding of a body of elastomeric composition within a mold cavity, around a core member and against the prepared surface of a test substrate, such as a ceramic or metallic disk, at the base of the mold cavity. The molded elastomeric composition is molded as an axial-symmetrical frustro-conical body which tapers down to a uniformly thin layer between the test substrate surface and the flat undersurface of the core member, and the core member supporting the molded elastomeric body bonded to the test substrate are separable from the mold cavity for attachment to a conventional tension test machine for measuring the interfacial bond strength between the elastomer and the prepared surface of the test substrate.

14 Claims, 6 Drawing Sheets

MOLDING DEVICE AND METHOD FOR MEASURING THE BONDING STRENGTH OF ELASTOMERS

BACKGROUND OF THE INVENTION

1. Field of the Invention

The present invention relates to a novel molding method and device for use in measuring the bonding strength of elastomeric compositions to various prepared surfaces.

The advent of complex and high density electronic systems for ground, airborne and space applications has required the parallel development of packaging technology including the use of elastomers to protect electronic system from vibration, shock, temperature extremes, and as a dielectric medium to prevent voltage breakdown between the internal components or to the containment vessel walls. Meeting these requirements depends upon maintaining a viable bond between the elastomer and substrates, components and containment walls. This bond strength depends on the elastomer and the physical and/or chemical preparation of the bonding surface. Therefore accurate quantification of this bond strength is critical to the development of these new systems to withstand the dynamic forces and thermal contraction which place significant tension stresses on the interface between the elastomer and the surface to which it is bonded.

2. State of the Art

Previously, lap shear tests have been relied upon to assess the bond strength of elastomers with various surfaces. However, the physics of the interface dictate that the relationship between the lap shear test results and the ability to withstand tensile forces at the surface is in itself a function of the surface/elastomer bond, resulting in the need to measure the tensile bond strength directly. Classical methods which measure the tensile bond strength successfully are accurate only when the bonding material is fairly rigid and low strains are induced during the measurement. In this case, most of the loading is uniaxial, with the average and local internal stress in the material very close, and the bond fails at substantially below the tensile limit of most rigid test materials. However, in the case of elastomers, if there is a significant thickness of material between the elastomer support structure and the test sample, at typical bond strengths obtainable, significant triaxial strains and stresses occur in the elastomer due to the stretching or necking down effects which cause rupture failures in the elastomer prior to reaching critical stresses at the interface. Thus valid results are not obtainable. With this background and in light of the limitations of the prior art, the present invention was conceived.

A variety of different devices are known for determining the bonding strength of various adhesives, coatings and paints for various surfaces by compressing a coated substrate and then measuring the bonding strength as the ultimate separation force that the bond can resist after the adhesive is set or cured. Reference is made to the following U.S. Pat. Nos. for their disclosure of such devices: 3,628,378; 3,821,892; 4,567,758; 4,586,371; 4,606,225; 4,893,513, 5,313,841; 5,361,639; and 5,649,447.

None of the aforementioned patents deal with or solve the problem of the test material developing significant triaxial stress risers, or necking down, under the effects of the tension forces generated during separation, and therefore the devices of these patents are unsatisfactory for the accurate measurement of the bonding strength of non-rigid, rubbery elastomers to prepared surfaces.

SUMMARY OF THE INVENTION

The present invention relates to a novel self-aligning device and method for the injection molding and curing of a body of elastomeric composition within a mold cavity, around a core member having a flat undersurface, and against the prepared flat parallel surface of a test substrate, such as a ceramic disk, at the base of the mold cavity. A predetermined narrow space confines the elastomeric composition as a uniformly thin layer between the flat substrate surface and the parallel flat undersurface of the core member, and the core member supporting the molded, cured elastomeric body bonded to the substrate are separable from the apparatus for attachment to a conventional tension test machine for measuring the interfacial bond strength between the elastomer and the prepared surface of the test substrate.

The core member is a custom bolt, and the head of a standard bolt is then bonded to the undersurface of the test substrate by means of a strong adhesive to provide an axial assembly for attachment to the tension test machine. The tension test machine pulls the core/custom bolt and the standard bolt in opposite directions and provides a quantitative measurement of the force required to separate the elastomeric body from the prepared surface of the support, or ceramic disk, at the interface thereof, while the unique shape of the mass of the molded elastomeric body substantially reduces or eliminates triaxial strains and stresses and necking down or stretching of the thin elastomeric layer molded and cured against the surface of the test substrate, thereby preventing any internal rupture of the thin elastomer layer prior to separation at its interface with the test substrate.

THE DRAWINGS

DETAILED DESCRIPTION

Figure 1:
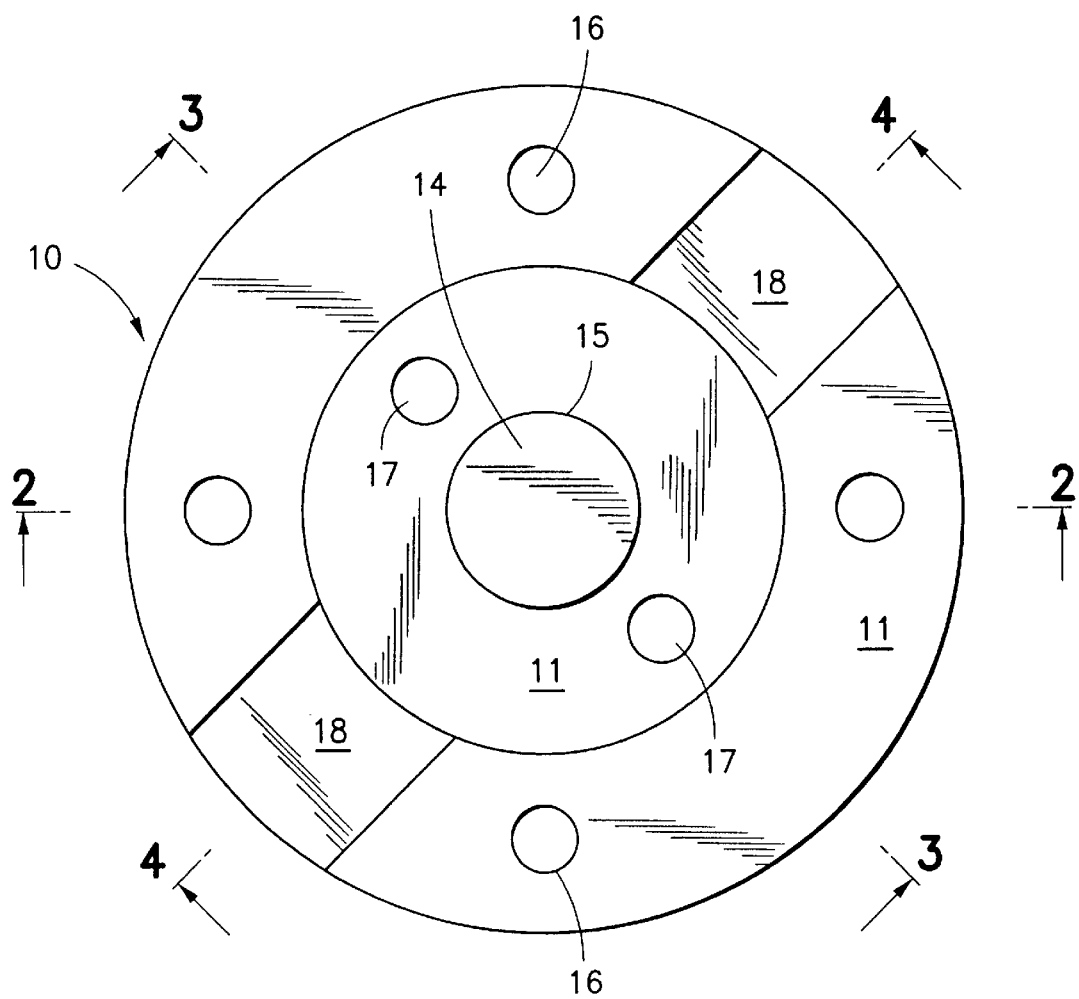
FIG. 1 is a plan view of an apparatus according to one embodiment of the present invention.

The present apparatus includes a multi-piece mold assembly 10 comprising a top section 11, a middle section 12, a bottom section 13 and a custom bolt/core member 14 having a threaded upper end which is engaged by the threaded bore 15 of the top section 11 to the limit of an annular stop flange 21 to align and position the core member 14. Sections 11 and 12 have central tubular openings to form a molding cavity 22 between their interior walls and the surface of the lower cylindrical core section 23, including its narrowed neck portion 24 and its head portion 26 having a flat undersurface 25. The upper surface of the bottom section 13 has a central recess or bore 27 for receiving a flat test substrate, such as a ceramic disk 28, to be bonded to an elastomer molded within the cavity 22. Disk 28 has parallel flat upper and lower surfaces.

Figure 2:
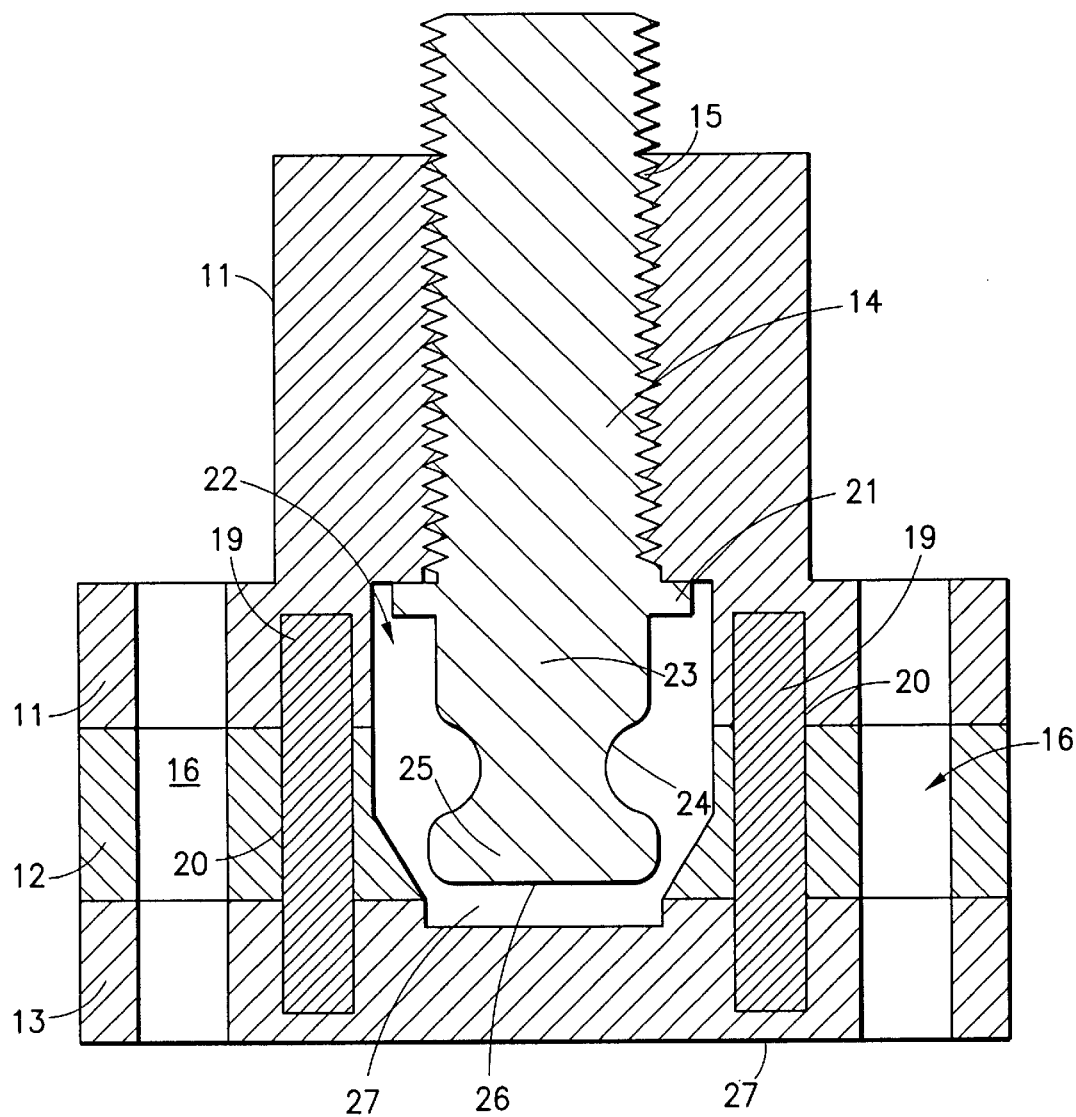
FIG. 2 is a cross-section taken along the line 2—2 of FIG. 1.
Figure 3:
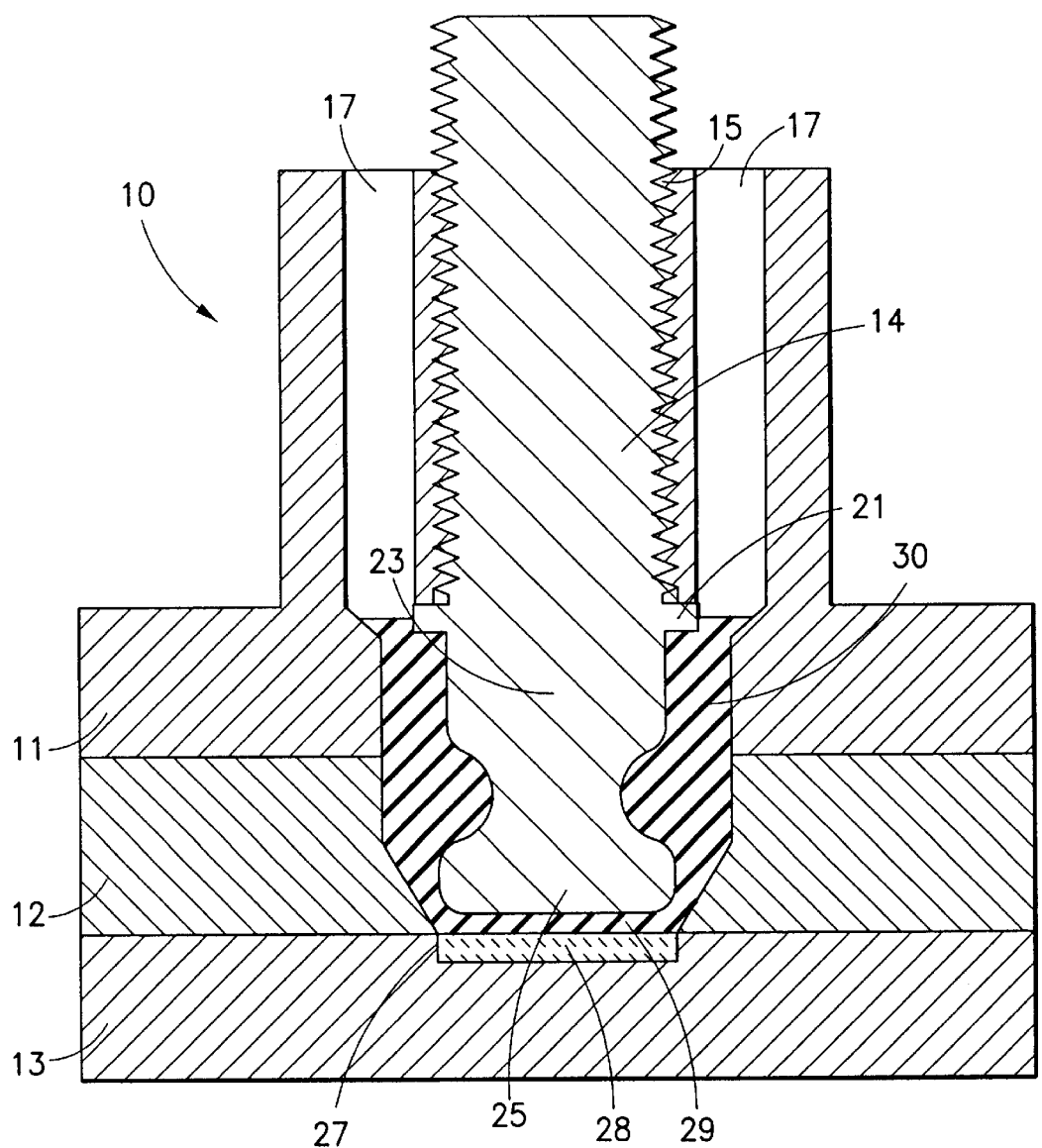
FIG. 3 is a cross-section taken along the line 3—3 of FIG. 1, but illustrating the mold cavity filled with elastomeric composition in contact with the prepared surface of a test substrate.
Figure 5:
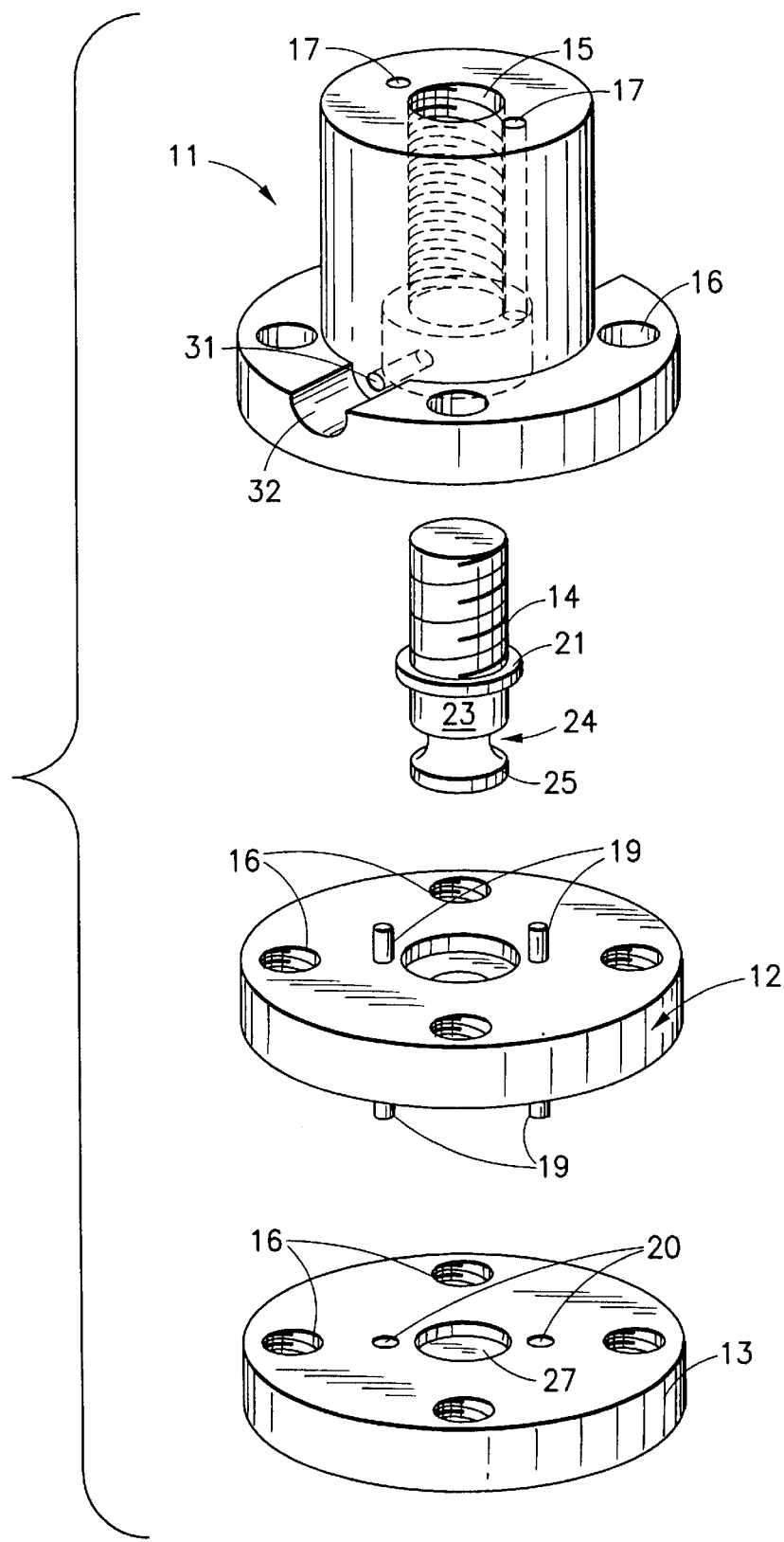
FIG. 5 is a perspective view of the apparatus of FIG. 1 with the elements thereof shown in spaced relation for purposes of illustration.

The assembly 10 includes an opposed pair of alignment pins 19 which fit within alignment bores 20 in the sections 11, 12 and 13, as shown by FIGS. 2 and 5, to facilitate the alignment of the bolt holes 16 for the reception of locking bolts (not shown) to secure the sections together during molding of the elastomeric composition injected through longitudinal filling ports 17 to fill the mold cavity 22 after the test disk 28 has been positioned within the bore 27, as shown in FIG. 3.

FIG. 3 illustrates the assembly 10 after curable liquid elastomeric composition 30 has been injected through the fill ports 17 to fill the mold cavity 22 and form a uniformly thin layer 29 between the flat undersurface 26 of the head 25 of the core member 23 and the parallel flat upper surface of the disk 28 which fills the bore 27 in the bottom section 13 of the mold.

Figure 4:
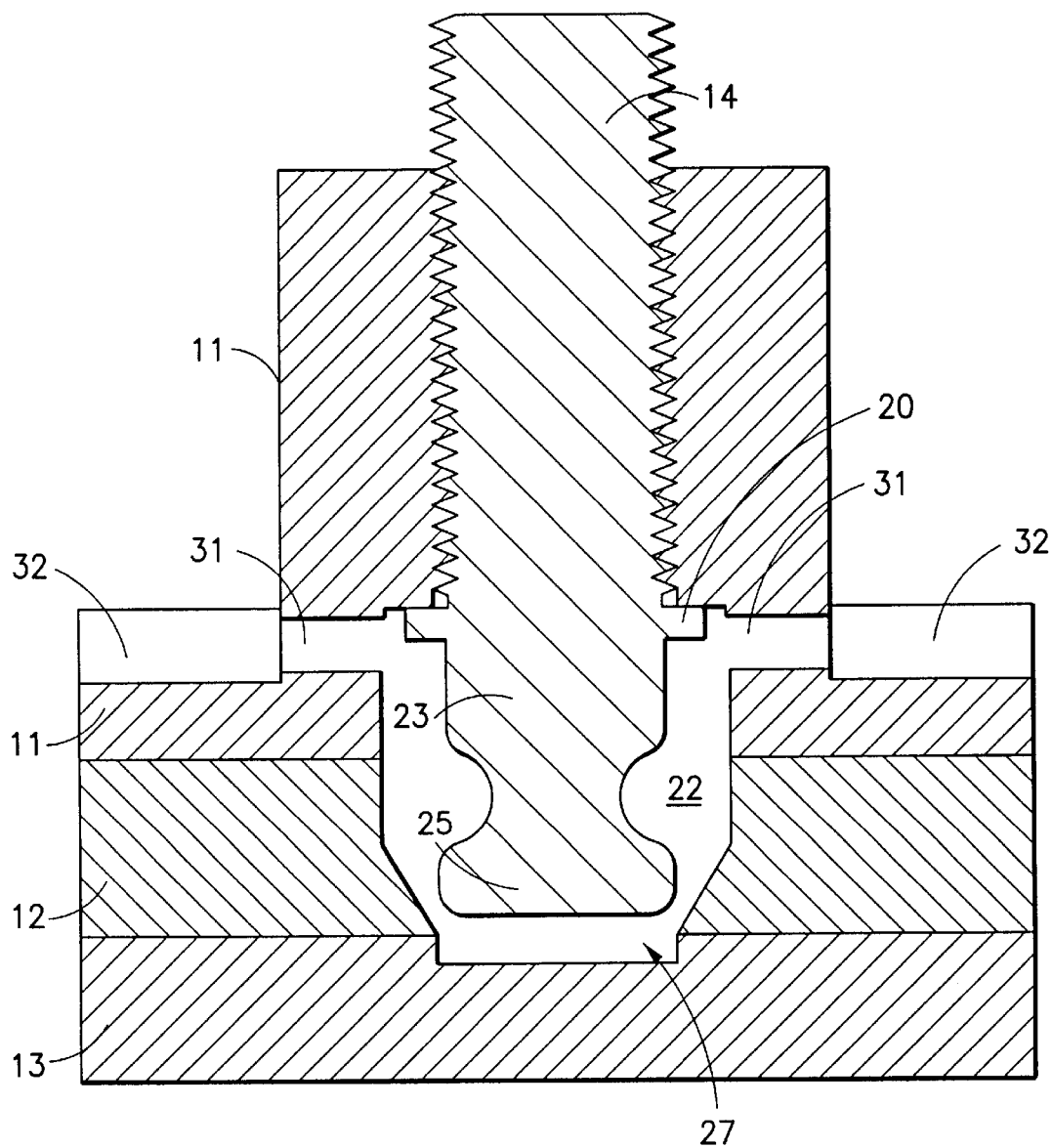
FIG. 4 is a cross-section taken along the line 4—4 of FIG. 1.

As shown by FIGS. 4 and 5, the top section 11 of the mold assembly is provided with overflow ports 31 (internal) and overflow channels 32 (external) which control the level of the uncured liquid elastomeric composition admitted to the mold cavity 22 through the filling ports 17, shown in FIG. 3. As illustrated by FIG. 5, the custom bolt 14 threadably engages the bolt hole 15 within the top section 11 of the assembly and is screwed in until the annular stop flange 21 engages the undersurface of 11 adjacent the entry of the hole 15, as shown in FIGS. 2, 3 and 4, to align and fix the position of the assembled core member.

Next, a test substrate, such as a ceramic or other test disk 28 having a prepared flat test surface is inserted into the central recess or bore 27 in the upper surface of the bottom section 13. Then the top, middle and bottom sections 11, 12 and 13, respectively, are assembled by aligning the pins 19 of the middle section with the alignment openings 20 in the underside of the top section 11 and in the upperside of the bottom section 13 and pressing the sections together. Bolts (not shown) are inserted through the openings 16 in the three sections to fasten the sections together as an assembly. The assembly is filled with uncured liquid elastomer which flows into the mold cavity 22 to encase the core section 23, neck section 24 and head portion 25 of the custom bolt 14 and form a thin uniform layer 29 between the flat undersurface 26 of the head portion 25 and the flat prepared upper surface of the test disk 28 contained within the central bore 27 of the bottom section 13.

Preferably the surface of sections 11 and 12 forming the outer walls of the mold cavity 22 are previously sprayed with a mold release agent in order to facilitate the separation of the cured axial-symmetric elastomer body 30 from the walls of the mold cavity 22. Curing is generally accomplished by heating the filled assembly to crosslink the elastomer and produce a solid rubbery mass which is strongly bonded to the core portion 23 of the custom bolt 14 and form a thin uniform layer 29 between the flat undersurface26 of the head portion 25 and the flat prepared upper surface of the test disk 28 contained within the central bore 27 of the bottom section 13.

Preferably the outer openings of the overflow ports 31 are sealed with plugs sprayed with mold release agent after the mold cavity 22 is filled and prior to the curing step to prevent leakage of the liquid elastomer. In many cases, the elastomer's un-cured mixture is very thick and viscous requiring significant flow channel width to reach and fill the cavity next to the test sample. This is the case for silicone rubbers, where passages on the order 0.030 inches are needed to achieve complete fill of the un-cured material.

Figure 6:
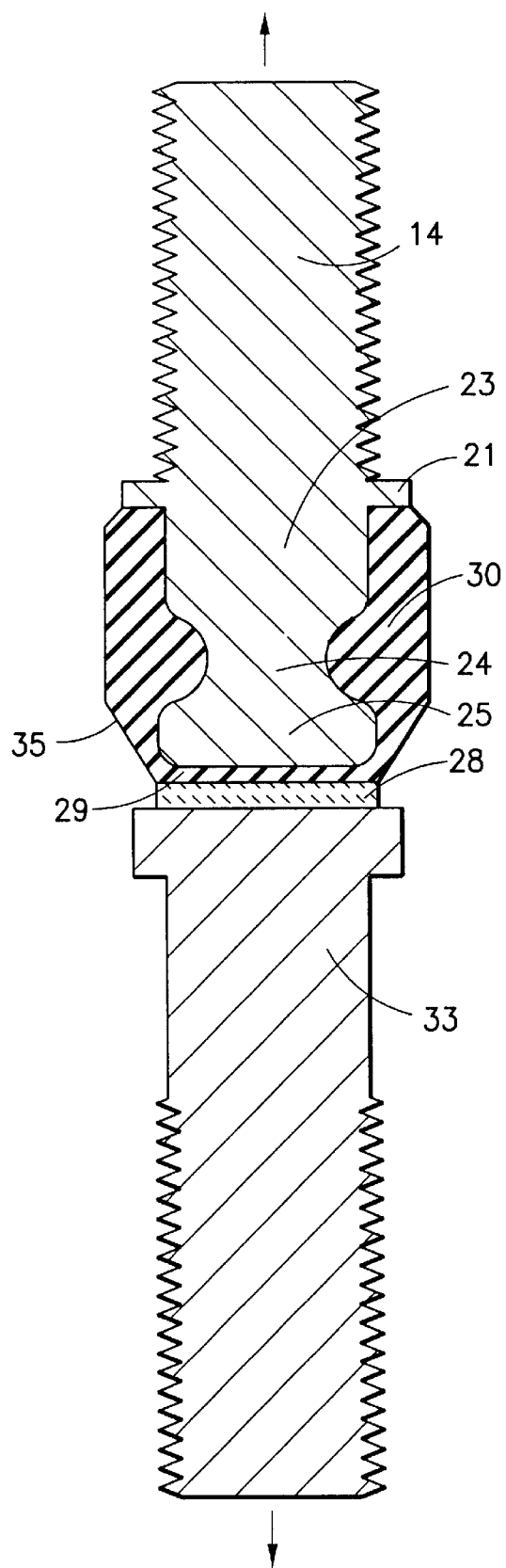
FIG. 6 is a side view of the core member/custom bolt with molded elastomeric body and test substrate bonded in axial relation to the head of a standard bolt, for attachment to a standard tension test machine.

After curing, the assembly 10 is disassembled by removing the fastening bolts from holes 16, separating the sections 11, 12 and 13, and unscrewing the custom bolt 14 carrying the cured solidified elastomer body 30 and bonded test disk 28, as illustrated by FIG. 6.

The flat side opposite the parallel prepared surf-ace of the disk 28 is then attached with strong adhesive to the flat head of a standard bolt 33 oriented in the opposing direction of the threaded custom bolt 14 as shown in FIG. 6. This axial assembly is then placed in a conventional tension loading test machine to determine the interface bond strength of the cured elastomer with the test surface. The unique and novel shape of the potted portion of the assembly formed by the present invention allows application of tensile stresses close to the value of the elastomer itself by preventing formation of significant internal tri-axial risers in the elastomer as the tension forces are transferred through the test structure.

The cured elastomer body 30 on the core section 23 has an axial-symmetric frustro-conical shape and a frustrum 35 which tapers down to the lower outer circumferential edge of the cured elastomer layer 29, as illustrated by FIG. 6. This unique shape produces a radial outward stress component which effectively cancels inward necking and peel stresses under tensile loading and allows application of pure tensile stresses and measurement of the tensile bond strength at the interface of the layer 29 and the surface of the test disk 28.

A convenient test sample consists of a round disk 28 of the test material, usually composed of ceramic or metal for electronic applications, which are on the order of 0.250 inches to 0.500 inches in diameter. With a minimum elastomer layer 29 in the range of 0.030 inches thick cured and bonded to one side of the test sample, an aspect ratio of sample diameter to elastomer thickness of 8.3 to 16.6 would be present. This would correspond to sample diameter to thickness of the bonded elastomer ranging from eight to sixteen to one.

If the elastomer body consisted simply of a cylinder of elastomer rubber 0.030 inches thick cast between the test sample with the prepared surface and an opposing bond surface, at typical bond strengths achievable of 50 to 130 percent of the elastomers modulus of elasticity, axial strains of 50 to 130 percent would also be reached. This would produce severe necking down of the material in the radial direction, causing significant peeling stresses, giving erroneous results.

However, according to the present invention, the unique shape of the annular mold cavity 22, angled up and outward away from the top of the outer circumferential edge of the cured elastomer maintains a radial outward stress component which effectively cancels inward necking and peel stresses and allows application of pure tensile stresses and accurate measurement of the tensile bond strength at the interface.

Thus, the present invention consists of a uniquely shaped three piece mold apparatus, with the test sample disk inserted in a holding and positioning cavity located in the top surface of the lower section. The center section of the mold includes an axial-symmetric annular cavity which reduces in diameter in its lower part and expands to a larger diameter in its upper part. The center section cavity receives a custom bolt which is threaded into the top section of the three part mold, and positioning pins align the top and bottom mold sections to the center mold section allowing accurate positioning of the center core body of the custom bolt in the axial-symmetric cavity, with the tread allowing accurate vertical positioning and alignment of the center core. The elastomer is introduced through top fill holes, and all surfaces that will contact the elastomer are previously sprayed with mold release agent. After cure of the elastomer, the lower section 13 and center section 12 are removed and the center core section 23 having the molded elastomer body 30 attached to the test sample disk 28 is unscrewed from the upper mold section 11 of the assembly 10. The opposite flat surface of the test sample disk 28 is then attached with strong adhesives to the head of a standard bolt 33 pointing opposite the direction of the custom bolt 14 and the unit placed in a conventional tension test machine for testing. The unique and novel frustro-conical shape of the potted portion or elastomer body 30 formed according to the invention allows application of the bonding tensile stresses close to the value of the elastomer itself by preventing formation of significant tri-axial stress risers in the thin elastomer layer 29 as the tension forces are transferred through the test structure.

The mold sections 11, 12 and 13 are formed from aluminum or other suitable mold material, and the test sample disk 28 is formed from ceramic or other material, the bonded surface of which is physically and/or chemically prepared in known manner to provide for high bond strength with the thin layer 29 of the elastomer, which is molded and cured as an axial-symmetrical mass 30.

The custom bolt 14 and the standard bolt 33 are formed from hardened steel or other suitable metal. The custom bolt 14 has its core section 23 contoured with a narrowed neck section 24, to provide a strong holding power for the cured molded elastomer mass 30, and with a wider lower head section 25 having a flat undersurface 26, parallel to the flat prepared upper surface of the test sample disk 28, to provide a uniform narrow gap therebetween into which the liquid uncured elastomeric composition flows and cures to form a thin elastomer layer 29 of the mass 30 which is strongly bonded to both the core head 25 and the disk 28. This configuration prevents the formation of significant triaxial stress risers in the elastomer layer 29 as the test machine applies tension forces in opposite directions until the elastomer layer is clearly separated from the prepared surface of the test sample disk 28 at a force measured by the tension test machine.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A device for molding an elastomeric composition against a surface of a test material within a mold cavity for purposes of measuring bonding strength therebetween in a conventional tension test machine, comprising a cylindrical assembly comprising a top mold section having an upper collar portion having a threaded central axial bore opening into a lower annular portion forming an axial-symmetric mold cavity portion; a central annular mold section having a center bore forming an axial-symmetric frustro-conical mold cavity portion; a bottom mold section having a central recess for retaining a sample of test material having parallel flat upper and lower surfaces, with the flat upper surface in communication with said mold cavity, and an elongate custom bolt element having a threaded upper shaft portion which engages the threaded bore of the collar portion for assembly into molding position, and having a lower mold core portion having a flat undersurface, said core portion extending axially to a fixed position centered within said mold cavity when said top, central and bottom mold sections are assembled to enclose and form an axial-symmetric frustro-conical mold cavity within which the flat undersurface of the core portion is parallel to and closely-spaced from the flat upper surface of the sample of test material; and filling port or ports in said top mold section for injecting curable liquid elastomeric composition to fill said mold cavity, surround said mold core portion and uniformly contact the upper surface of a sample of test material retained in the central recess of the bottom section, whereby the injected elastomeric composition is cured to a solid elastomeric state, the mold sections are separated from each other and the custom bolt element is unscrewed from the top mold section as a bolt carrying an axial-symmetric frustro-conical molded body of the cured elastomeric composition bonded to the sample of test material for evaluating the strength of the bond therebetween in said conventional tension test machine, the frustro-conical shape of said molded body of elastomeric composition avoiding significantly axial strains caused by necking down or stretching of the elastomeric composition in said test machine.

2. A device according to claim 1 in which said mold sections include means aligning said sections in assembly.

3. A device according to claim 2 in which the alignment means comprise alignment holes and alignment pins.

4. A device according to claim 1 in which said mold sections include means for locking said sections in assembly.

5. A device according to claim 4 in which said locking means comprise bolts engaged within holes in each of said mold sections.

6. A device according to claim 1 in which said filling port or ports comprise longitudinal passage or passages through the collar portion of the top mold section, adjacent the central axial bore, opening into the mold cavity portion.

7. A device according to claim 1 in which said elongate custom bolt element further comprises a flange ring between the upper shaft portion and the lower mold core portion to provide a molding position stop means when the upper shaft section is screwed into the threaded bore of the top section from within the lower annular section thereof.

8. A device according to claim 1 in which said top mold section further comprises at least one overflow means for releasing any excess curable elastomeric composition from the mold cavity during the filling thereof.

9. A device according to claim 8 in which said overflow means comprise transverse bores through the lower annular portion of the top mold section opening into the mold cavity.

10. A custom bolt element for use in evaluating the bonding strength of cured elastomeric compositions to a surface of a test material while avoiding significant triaxial strains caused by necking down or stretching of the elastomeric composition, comprising an elongate bolt element having a threaded end which is engageable within a conventional tension test machine, and having a mold core end having molded thereon an axial-symmetrical frustro-conical mass of cured elastomeric composition bonded by a uniformly-thin layer of said elastomeric composition to one surface of a body of test material, and a standard bolt opposed in direction to said elongate bolt element and having a head, an opposed surface of the body of test material being more-strongly bonded to said head of said standard bolt, to enable pulling forces to be applied to the test material from opposite directions, the frustro-conical shape of said molded body of elastomeric composition avoiding significantly axial strains caused by necking down or stretching of the elastomeric composition under the effects of said pulling forces.

11. A custom bolt element according to claim 10 in which the mold core end has a narrowed neck portion adjacent a wider head portion having a flat undersurface carrying said thin layer of the elastomeric composition.

12. A custom bolt element according to claim 10 comprising a flange portion between said threaded end and said mold core end.

13. A method for reducing internal triaxial stresses and stretching of an elastomeric composition while measuring tensile bond strength between said elastomeric composition and a surface of a test substrate, which comprises molding an axial symmetrical frustro-conical body of said elastomeric composition adjacent a core end of a test bolt, the other end of which is attachable to a conventional tension test machine, said core end of the test bolt having a head portion having a flat undersurface closely spaced from the parallel flat surface of a test substrate so that the frustro-conical body of elastomeric composition tapers down to and forms a thin layer therebetween, and curing the elastomeric body including said thin layer bonded to the surface of the test substrate, the frustro-conical shape of said body of said elastomeric composition preventing stretching and internal rupture of the thin layer are prevented during the application of separation forces to the interface thereof with the surface of the test substrate in a conventional tension test machine.

14. Method according to claim 13 in which the core end of the test bolt comprises a narrowed neck portion adjacent a wider head portion for retaining the body of molded elastomeric composition on said core end of the test bolt under the effects of the separation forces applied in the tension test machine.

\* \* \* \* \*